(12) United States Patent
Kasza

(10) Patent No.: US 6,413,444 B1
(45) Date of Patent: Jul. 2, 2002

(54) METHODS AND APPARATUS FOR PRODUCING PHASE CHANGE ICE PARTICULATE SALINE SLURRIES

(75) Inventor: Kenneth E. Kasza, Palos Park, IL (US)

(73) Assignee: The University of Chicago, Chicago, IL (US)

( * ) Notice: Subject to any disclaimer, the term of this patent is extended or adjusted under 35 U.S.C. 154(b) by 24 days.

(21) Appl. No.: 09/586,576

(22) Filed: Jun. 2, 2000

Related U.S. Application Data

(60) Provisional application No. 60/146,753, filed on Aug. 2, 1999.

(51) Int. Cl.[7] ............................. F25C 1/00; C09K 5/02
(52) U.S. Cl. ............................ 252/70; 62/66; 62/68; 62/75; 62/340; 62/540
(58) Field of Search .................... 252/70, 71; 106/13; 62/66, 68, 75, 540, 340

(56) References Cited

U.S. PATENT DOCUMENTS

| | | | | |
|---|---|---|---|---|
| 3,069,866 A | * | 12/1962 | Dunn | 62/136 |
| 3,180,110 A | * | 4/1965 | Dunn | 62/343 |
| 3,987,211 A | * | 10/1976 | Dunn et al. | 426/551 |
| 4,596,120 A | * | 6/1986 | Knodel et al. | 62/59 |
| 4,750,336 A | * | 6/1988 | Margen | 62/434 |
| 4,914,921 A | * | 4/1990 | Knodel | 62/59 |
| 6,244,052 B1 | * | 6/2001 | Kasza | 62/1 |

FOREIGN PATENT DOCUMENTS

JP       11-335660    * 12/1999

OTHER PUBLICATIONS

Copending provisional application by Kenneth E. Kasza et al., filed Aug. 2, 1999, provisional application No. 60/146,753 and entitled Method for Inducing Hypothermia.

* cited by examiner

*Primary Examiner*—Anthony Green
(74) *Attorney, Agent, or Firm*—Joan Pennington

(57) ABSTRACT

A phase change particulate saline slurry and methods and apparatus are provided for producing phase change particulate saline slurries. One method for producing phase change particulate saline slurries includes the steps of providing a liquid with a set percentage freezing point depressant, such as, a set percentage saline solution; subcooling the saline solution to a freezing point to produce ice particles; and increasing an ice particle concentration under controlled temperature for a period of time to provide a set ice particle concentration for the phase change particulate saline slurry. In another method for producing phase change particulate saline slurries, water and a first set amount of sodium chloride are provided to produce a saline solution. The saline solution is cooled to a set temperature. A selected percentage of chunk ice is added to the saline solution and the chunk ice is broken into ice particles. The ice particles have a small size. Next a second set amount of sodium chloride is added and distributed for smoothing of the ice particles. The total saline solution concentrations resulting from the total of the first set amount and the second set amount of added sodium chloride are preferably in the range of about 0.5% to 6.0%. The loadings or percentage of ice particles are preferably in the range of 5% to 50%. A phase change particulate saline slurry includes a water and sodium chloride solution. The sodium chloride is provided in a range between about 0.5% to 6.0%. A percentage of ice particles is provided in the range between about 5% to 50%. The ice particles have a size of about 1 mm or less than 1 mm; and the ice particles have a generally smooth shape.

7 Claims, 3 Drawing Sheets

METHODS AND APPARATUS FOR PRODUCING PHASE CHANGE ICE PARTICULATE SALINE SLURRIES

This application claims the benefit of prior filed copending provisional application filed Aug. 2, 1999, by Kenneth E. Kasza et al., provisional application number 60/146,753 and entitled METHOD FOR INDUCING HYPOTHERMIA. The subject matter of the above-identified copending provisional application is incorporated herein by reference.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to methods and apparatus for producing phase change ice particulate saline slurries of very high fluidity, cooling capacity and stability.

DESCRIPTION OF THE RELATED ART

Phase change slurries in the form of high concentrations of small ice particles in a liquid carrier have dramatically increased coolant capacity as compared to other liquids such as single phase water or other liquids involving no heat of fusion effects. Phase change ice slurries developed by the present inventor Kenneth E. Kasza have been used for cooling in large building complexes. The development of ice slurries by the inventor for cooling buildings has shown that ice particles suspended in water or other carrier liquid, if engineered to have the correct characteristics, can be pumped as readily as water and are stable for significant periods of time without agglomeration where ice particles freeze together or entangle in clusters. The cooling capacity of such a slurry can be 5 to 10 times, depending on the particular loading in the carrier liquid, that of an equal amount of water which exhibits only sensible heat cooling capacity. For use in cooling buildings, the particles preferably are small relative to the conduit diameter, not loaded to a level of more than 30% ice in order to enhance delivery to the target cooling zone, and relatively smooth to avoid particle entanglement and formation of large clusters. Small additions of certain types of chemicals, such as freezing point depressants, when added to a slurry during an appropriate time when making the slurry, have been shown to dramatically improve the fluidity and storability of the slurry by altering the microscale features (smoothing) of the individual particles comprising the slurry.

A need exists for an improved method and apparatus for producing phase change particulate saline slurries. It is desirable to produce phase change particulate saline slurries, with high cooling capacity, fluidity, and storability, for example for use to induce targeted protective hypothermia of human organs/tissue during medical treatment.

It is an object of the present invention to provide methods and apparatus for producing phase change particulate saline slurries.

It is an object of the present invention to provide an improved phase change particulate saline slurry.

SUMMARY OF THE INVENTION

In brief, a phase change particulate saline slurry and methods and apparatus are provided for producing phase change particulate saline slurries. One method for producing phase change particulate saline slurries includes the steps of providing a liquid with a set percentage freezing point depressant to form a first solution, such as, a set percentage saline solution; cooling the first solution to a set temperature to produce ice particles; and increasing an ice particle concentration under controlled temperature for a period of time to provide a set ice particle concentration for the phase change particulate saline slurry.

In another method for producing phase change particulate saline slurries, water and a first set amount of sodium chloride are provided to produce a saline solution. The saline solution is cooled to a set temperature. A selected percentage of chunk ice is added to the saline solution and the chunk ice is broken into ice particles. The ice particles have a small size. Next a second set amount of sodium chloride is added and distributed for smoothing of the ice particles.

A phase change particulate saline slurry includes a water and sodium chloride solution. The sodium chloride is provided in a range between about 0.5% to 6.0%. A percentage of ice particles is provided in the range between about 5% to 50%. The ice particles have a size of about 1 mm or less than 1 mm; and the ice particles have a generally smooth shape.

In accordance with features of the invention, the total saline solution concentrations resulting from the total of the first set amount and the second set amount of added sodium chloride are preferably in the range of about 0.5% to 6.0%. The loadings or percentage of ice particles are preferably in the range of 5% to 50%. The resulting slurry if to be stored for later use is stored in a highly insulated container to reduce melt out of ice particles and temperature gradient in the stored slurry which can cause ice particle freezing together and reduce fluidity.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
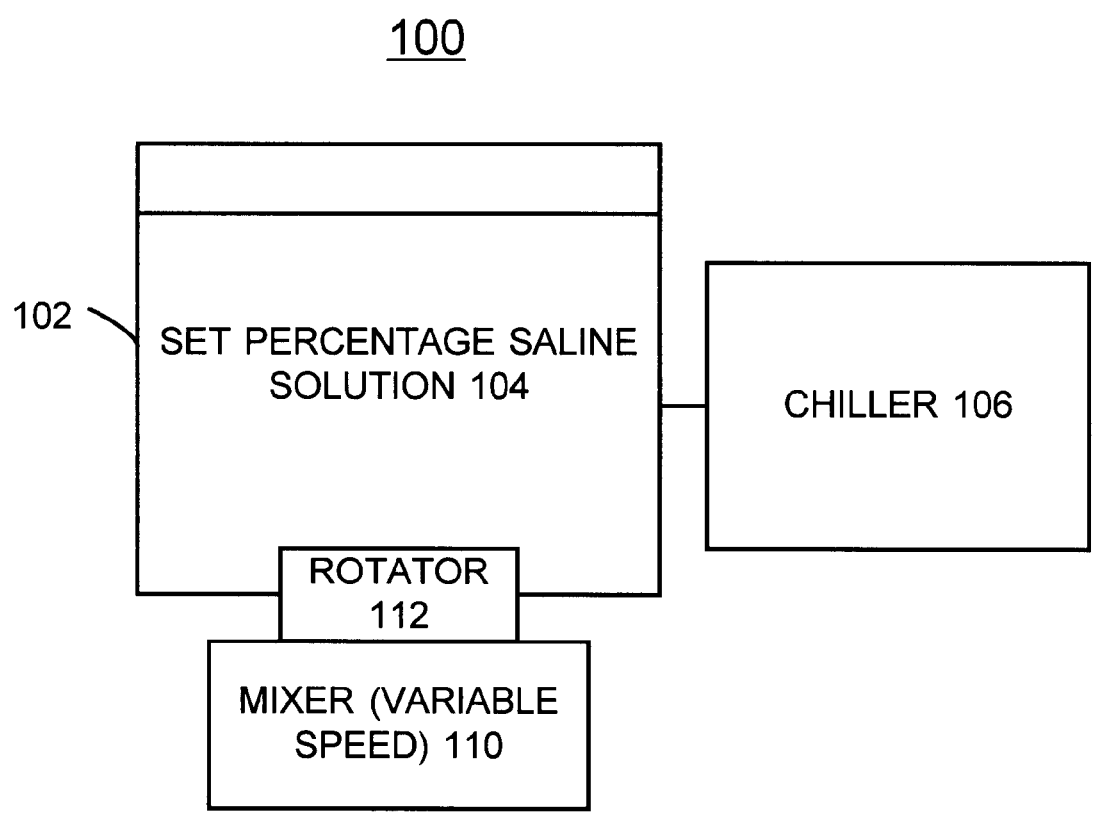
FIG. 1 is a block diagram representation illustrating exemplary apparatus for producing phase change particulate saline slurries.

Having reference now to the drawings, in FIG. 1 there is shown apparatus for producing phase change particulate saline slurries in accordance with an embodiment of the invention and generally designated by reference character 100. A container 102 contains a selected percentage saline solution 104. A chiller device 106 is provided for cooling the saline solution 104. A mixer 110 and an associated rotator 112, such as a variable speed mixer or blender, is provided for processing the phase change particulate saline slurries in accordance with methods illustrated and described with FIGS. 2 and 3. The method illustrated and described with respect to FIG. 3 is the preferred embodiment of the invention.

In accordance with features of the invention, saline solution concentrations are preferably in the range of about 0.5% to 6.0% and the loadings, or percentage of ice particles, are preferably in the range of 5% to 50%. The phase change particulate saline slurry of the preferred embodiment is stable or storable, fluid and highly loaded ice particle medical grade slurry. A phase change particulate saline slurry of the preferred embodiment advantageously can be used to induce targeted protective hypothermia during medical treatment. The medical use of slurries for cooling in general requires slurries of higher fluidity than those currently used in building cooling due to the smaller diameter of slurry delivery tubing, needles and organ/blood vessel flow passages.

In accordance with features of the invention, both chemical and thermal alteration of ice particles can be used together or individually. By introducing a small amount of thermally induced ice particle melting, such as by adding a warmer fluid at an appropriate time during slurry particle formation, produces beneficial particle smoothing. The improved slurries of the invention are based upon developments of ice slurries by the inventor at Argonne National Laboratory.

Figure 2:
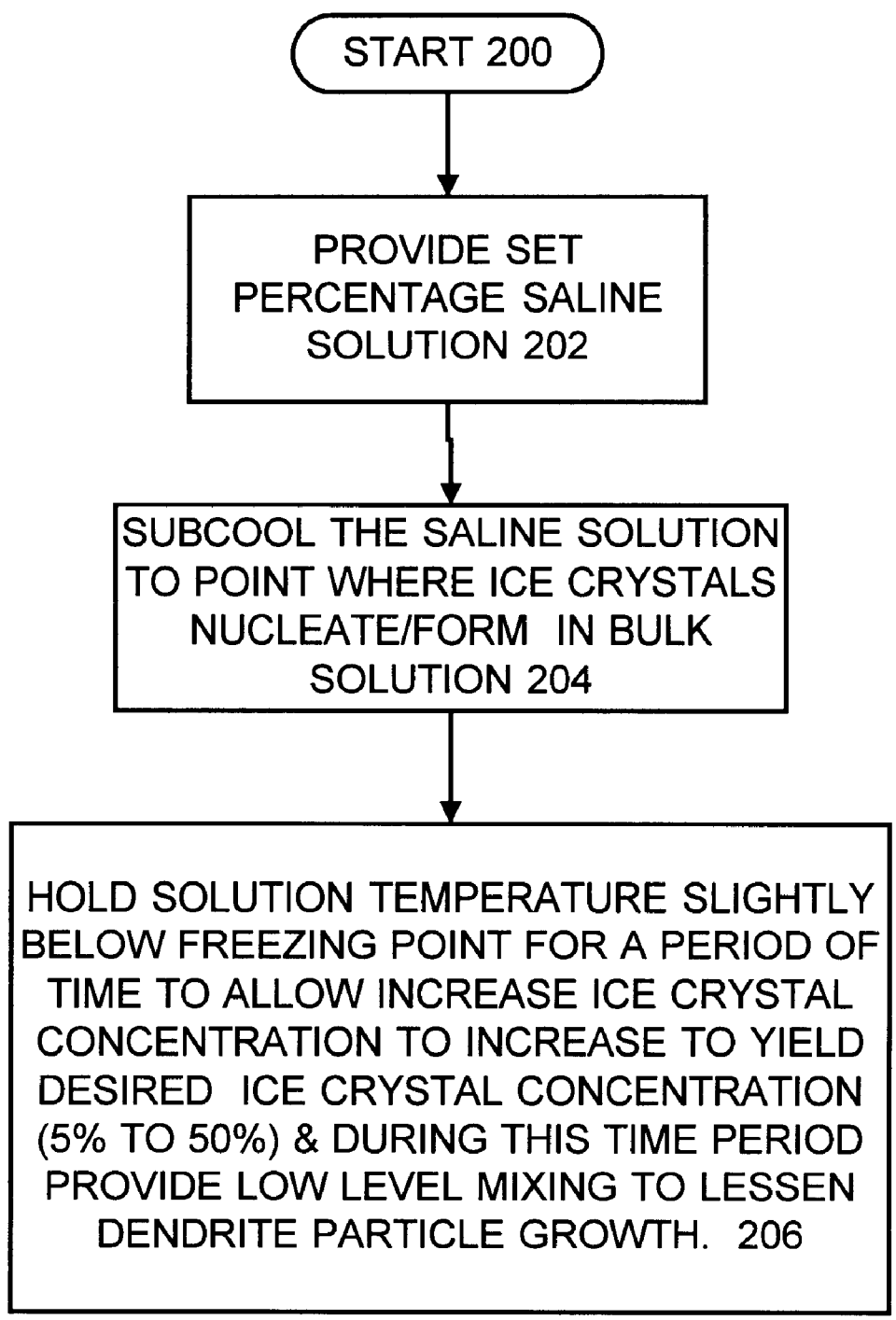
FIG. 2 is a flow chart illustrating exemplary steps for producing phase change particulate saline slurries.
Figure 3:
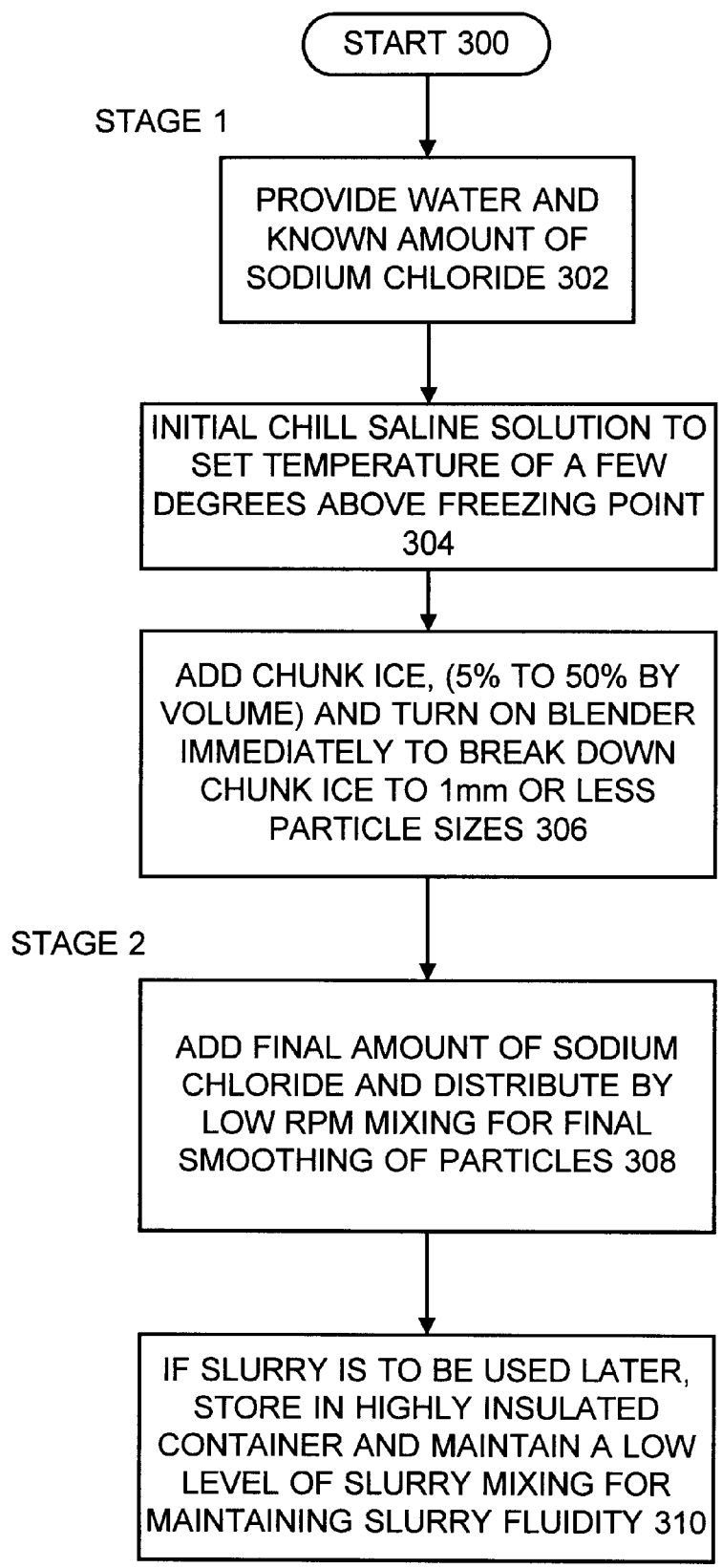
FIG. 3 is a flow chart illustrating exemplary steps for producing phase change particulate saline slurries in accordance with a preferred embodiment of the invention.

Referring to FIG. 2, there are shown exemplary steps for producing phase change particulate saline slurries in accordance with a first embodiment of the invention starting at a block 200. First a set percentage saline solution or other freezing point depressant is provided to form a first solution as indicated in a block 202. For example, the saline solution is a sodium chloride aqueous solution serving as a freezing point depressant. The saline solution alters the nature of the ice crystals formed during the subcooling stage of the solution and subsequent flash freezing which causes homogenous ice particle nucleation/formation in the bulk solution when the solution is subcooled to below its freezing point. Using, for example, a 0.9% saline solution, a slurry can be formed both in saline solution confined in a container or directly in a plastic medical IV injection bag. The saline solution is cooled to a point where ice crystals form as indicated in a block 204. For the 0.9% saline solution, the freezing point for this concentration of sodium chloride is −0.5° C. In contrast to pure water, the saline solution in the beaker and the medical injection bag forms very small separated ice crystals of size less than 0.1 mm initially. These very small ice crystals grow to approximately 0.2 mm or 0.3 mm as the ice crystal loadings grows with time after initial nucleation of the solution under a low level of agitation or mixing. The slurry is allowed to increase in ice crystal concentration for a set period of time while providing low level mixing to lessen dendrite particle growth, for example, about 15 minutes, yielding a selected ice crystal concentration of approximately 5% to 50% as indicated in a block 206. In the produced slurry, the ice particles are generally smaller and less dendritic than if formed in pure water due to the presence of the sodium chloride. This slurry readily flows through 3 mm diameter tubing.

Referring to FIG. 3, there are shown exemplary steps for producing phase change particulate saline slurries in accordance with another preferred embodiment of the invention starting at a block 300. In a first stage, water and a known amount of sodium chloride or another type of freezing point depressant or combinations thereof, are provided to provide a desired saline solution as indicated in a block 302.

For example, the amount of sodium chloride may be in a range between about 0.5% weight of sodium chloride to 5% weight of sodium chloride in water. The more sodium chloride used provides a lower freezing point of the solution. At 0.5% by weight of sodium chloride in water, the equilibrium temperature is approximately −0.3° C. At 5% by weight of sodium chloride in water, the equilibrium temperature is approximately −4° C. to −5° C. The more sodium chloride used provides smoother ice particles up to a point of diminishing returns which depending on particle initial roughness is in the range of 4%–7%.

Next the saline solution produced at block 302 is chilled to a set temperature, such as several degrees above the freezing point of the saline solution for example, approximately 7° C. to 10° C. as indicated in a block 304. This cooling step facilitates mixing and thermal induced smoothing of small particles formed during ice chunk break down to the particle size needed for the application. Then chunk ice is added, for example 50% by volume and a high speed blender is turned on immediately to break down the chunk ice to particles of a size of 1 mm or less as indicated in a block 306. The very small ice particles have a generally smooth, globular or spherical shape with some remaining particle roughness.

In a second stage as indicated in a block 308, a final amount of sodium chloride is added and the blender is turned on for low speed mixing to prevent additional particle break down and to distribute the added sodium chloride into the slurry for final smoothing of the small ice particles. If the slurry is to be used later, the slurry is stored in a highly insulated container while maintaining low level of slurry mixing for maintaining optimum slurry fluidity as indicated in a block 310.

In accordance with features of the invention, the two stage process of FIG. 3 produces an improved phase change particulate saline slurry that readily flows through a 14 GA needle. This improved phase change particulate saline slurry readily flows through plastic tubing as small as 1 mm in diameter. The total saline solution concentrations resulting from the total amount of added sodium chloride at blocks 302 and 308 are preferably in the range of about 0.5% to 6.0%. The loadings, or percentage of ice crystals, are preferably in the range of 5% to 50%. The first method of FIG. 2 produces more elongated and dendritic, rough particles which render the slurry of lower fluidity, but depending on use can be adequate. It should be understood that the present invention is not limited to the use of a sodium chloride saline solution. The methods of the invention are applicable to slurries involving water and other types of freezing depressants, various saline solutions with other types of salts or combinations. For medical treatment, the chemicals must be compatible with human organs/tissue.

While the present invention has been described with reference to the details of the embodiments of the invention shown in the drawing, these details are not intended to limit the scope of the invention as claimed in the appended claims.

What is claimed is:

1. A method for producing phase change particulate saline slurries comprising the steps of:
   providing water and a first set amount of sodium chloride to produce a saline solution;
   cooling said saline solution to a set temperature;
   adding a selected percentage of chunk ice to said saline solution and breaking said chunk ice into ice particles; said ice particles having a size of about 1 mm or less than 1 mm; and
   adding a second set amount of sodium chloride and distributing said added second set amount of sodium chloride for smoothing of said ice particles.

2. A method for producing phase change particulate saline slurries as recited in claim 1 therein said steps of providing water and a first set amount of sodium chloride to produce a saline solution and adding a second set amount of sodium chloride provide a saline solution in a range between about 0.5% to 6.0%.

3. A method for producing phase change particulate saline slurries as recited in claim 1 wherein said step of adding a selected percentage of chunk ice to said saline solution provides a percentage of ice particles in the range of about 5% to 50%.

4. A method for producing phase change particulate saline slurries as recited in claim 1 wherein said step of breaking said chunk ice into ice particles includes the step of utilizing a high speed blender and breaking said chunk ice into ice particles.

5. A method for producing phase change particulate saline slurries as recited in claim 1 wherein said step of cooling said saline solution to a set temperature includes the step of cooling said saline solution to a temperature above a freezing point of about 7° C. to 10° C. to provide thermal smoothing of particles during break down of said chunk ice.

6. A method for producing phase change particulate saline slurries as recited in claim 1 wherein said first set amount of sodium chloride and said second set amount of sodium chloride are approximately equal and together provide a saline solution in a range between about 0.5% to 6.0%.

7. Apparatus for producing phase change particulate saline slurries comprising:

a container for containing a saline solution including water and a first set amount of sodium chloride;

a cooler for cooling said saline solution to a set temperature;

means for adding a selected percentage of chunk ice to said saline solution and means for breaking said chunk ice into ice particles; said ice particles having a size of about 1 mm or less than 1 mm; and means for adding a second set amount of sodium chloride and means for distributing said added second set amount of sodium chloride for smoothing of said ice particles.

* * * * *